United States Patent [19]

Shay

[11] Patent Number: 4,786,801

[45] Date of Patent: Nov. 22, 1988

[54] FINISH LEAK DETECTOR HAVING VERTICALLY MOVABLE LIGHT SOURCE

[75] Inventor: Timothy W. Shay, Horseheads, N.Y.

[73] Assignee: Emhart Industries Inc., Farmington, Conn.

[21] Appl. No.: 60,701

[22] Filed: Jul. 21, 1987

[51] Int. Cl.⁴ .............................................. G01N 9/04
[52] U.S. Cl. ................................ 250/223 B; 356/240
[58] Field of Search ................... 250/223 B; 73/865.8, 73/865.9, 104; 209/524, 526, 538; 356/240

[56] References Cited

U.S. PATENT DOCUMENTS

| | | | |
|---|---|---|---|
| 3,089,594 | 5/1963 | Early | 250/223 B |
| 4,454,542 | 6/1984 | Miyazawa | 250/223 B |
| 4,606,635 | 8/1986 | Miyazawa et al. | 250/223 B |
| 4,701,612 | 10/1987 | Sturgill | 250/223 B |

Primary Examiner—David C. Nelms
Assistant Examiner—Stephone B. Allen
Attorney, Agent, or Firm—Arthur B. Moore

[57] ABSTRACT

An apparatus for inspecting the sealing surface of a container for dips, saddles and lean is disclosed. While the container is rotated, a beam of light is projected horizontally above and through a finish portion of said container. An optical detector detects the height of said sealing surface by detecting the location of a minimum in the light beam. Dips in the height indicate dips or saddles. Alternately, an opaque bearing member is lowered onto the sealing surface in the path of the light beam to provide a reference indicative of the prevailing height of the sealing surface. Light passing between the underside of the bearing member and the sealing surface indicates a dip or saddle.

4 Claims, 10 Drawing Sheets

FINISH LEAK DETECTOR HAVING VERTICALLY MOVABLE LIGHT SOURCE

BACKGROUND OF THE INVENTION

The invention relates generally to container inspection apparatus and deals more particularly with an apparatus for testing the sealability of the mouth of a container.

Two types of sealing surface defects are dips and saddles. A dip is a narrow depression in the bottle mouth and a saddle is a wide depression.

A wide variety of finish leak detectors were previously known such as those disclosed in U.S. Pat. Nos. 3,496,761 and 4,490,800. These detectors inspect the sealing surface of a bottle which is fed by a conveyor or auger screw to an inspection site located beneath the detector. The detector of U.S. Pat. No. 3,496,761 includes a test fitting which is lowered into engagement with the mouth of the bottle at the inspection site and forms an air-tight seal if the bottle mouth is properly formed—smooth, flat and generally horizontal; otherwise, a leak results. The sealability of the bottle mouth by the test fitting mimics the sealability of the bottle mouth by a cap or other type of commercial seal.

In various leak detectors previously known, air is injected into the bottle and pressure is sensed according to a variety of schemes. For example, in U.S. Pat. No. 3,496,761 a metered volume of air is injected into the container by a piston and cylinder assembly which forms a pump. At the conclusion of the discharge stroke of the piston and cylinder assembly, while the test fitting still closes the mouth of the container under test, the air pressure retained in the container is gauged to determine whether an excessive leakage takes place due to imperfections in the container mouth. While this system is effective in detecting flaws in the surface of a bottle mouth, it is limited in the rate at which it can inspect bottles. Moreover, this type of inspection system requires contact with the bottle and injection of air, and the fulfillment of each requirement may contaminate the bottle.

U.S. Pat. No. 3,555,980 to Mathias discloses another type of finish leak detection apparatus. The apparatus illuminates the rim of a bottle with a beam of radiant energy which is polarized so that it has an electric vector perpendicular to the top surface of the container. The container is rotated relative to the beam during inspection. Certain types of defects reflect a portion of the beam upwardly into a sensor which has its line of vision forming Brewster's angle with the direction of the beam. Because of the polarization and the angular relation, a defect makes a substantial reduction in the amount of radiant energy transmitted into the container.

U.S. Pat. No. 3,880,750 to Butler discloses another optical apparatus for inspecting the sealing surface of a glass container in which a light source focuses a thin line of light across the rim. A light sensor receives a deflection of this light from the rim to provide a reference level. A defect in the rim causes a rise or fall in the received light.

U.S. Pat. No. 4,026,414 to Ellinger discloses another optical apparatus for testing the sealing surface of a container in which a light sensing head made up of a mosaic of 30-40 light sensors in the form of a circular ring is supported above a bottle being inspected. A light source provides a beam through the central aperture which floods the mouth of the bottle and light is reflected upwardly from the bottle rim to the various sensors.

A general object of the present invention is to provide a detector to sense the sealability of a container mouth which detector is reliable and accurate and provides a high throughput.

SUMMARY OF THE INVENTION

The invention resides in an apparatus for inspecting the sealing surface of a container for dips, saddles and lean. While the container is rotated, a beam of light is projected above and through a finish portion of said container. According to one feature of the invention an optical detector detects the height of the sealing surface by detecting the location of a minimum in the light beam. Dips in the height indicate dips or saddles. According to another feature of the invention, an opaque bearing member is lowered onto the sealing surface in the path of the light beam to provide a reference indicative of the prevailing height of the sealing surface. Light passing beneath the underside of the bearing member and above the sealing surface indicates a dip or saddle.

DETAILED DESCRIPTION OF THE PREFERRED EMBODIMENT

Figure 1:
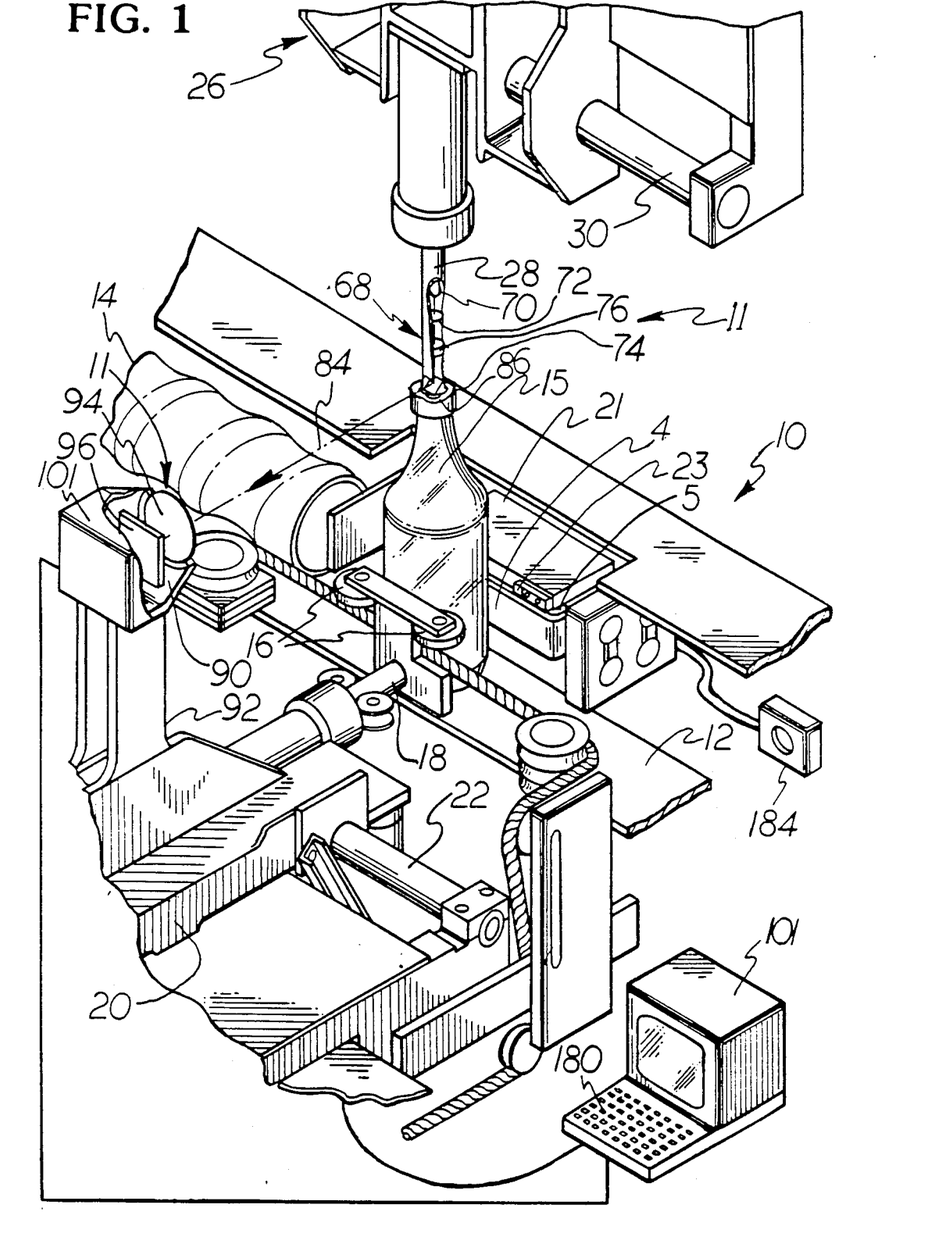
FIG. 1 is a perspective view illustrating an inspection system including a finish leak detector embodying the present invention.

FIG. 1 illustrates an inspection system generally designated 10 which includes a finish leak detector 11 embodying the present invention. A container 15 to be inspected is brought to the detector 11 on a linear conveyor 12 of conventional construction. The containers are spaced and sequentially moved into a test area or an inspection site by a feed screw 14. As the container 15 enters the test area, it is engaged by a pair of spaced rollers 16 on a horizontal plunger 18 mounted on a horizontally movable carriage 20. Carriage 20 is mounted for movement along the axes of shafts 22 (only one shaft is illustrated). While only one pair of rollers 16 is illustrated, use of two pairs of rollers disposed one above the other may be utilized more efficiently with certain types of containers.

The rollers 16 contact the container 15 and move it with the carriage 20 while pressing the container 15 against a horizontally moving endless belt 4. The belt 4 rotates the container 15 fast enough to make at least one full turn as it passes through the test area. The belt 4 extends around guide rollers 5 in housing 21 and is driven by a variable speed motor 17 (FIG. 3) whose speed can be adjusted to provide the required rotation. A brake block 23 of a material such as rubber and having a cam face is supported by housing 21. Block 23 and its angled cam face cause the container to loose contact with belt 4 and stop the container from rotating due to the pressure applied by rollers 16. Block 23 is located at the downstream end of the test area.

The belt 4 can move either opposite the direction of conveyor movement or with the direction of conveyor movement. The preferred direction is with conveyor movement to facilitate the discharge down the conveyor of defective bottles which may fracture during inspection.

A carriage 26 having a downwardly extending plunger 28 is reciprocally mounted for horizontal movement along shafts 30 (only one shaft is illustrated). The plunger 28 is mounted for vertical movement with respect to the carriage 26. The carriages 20 and 26 are moved in synchronism through the test area at constant speed in the direction of travel of the conveyor 12 and return at a substantially sinusoidal rate after completion of the inspection of the container 15. The mechanism for reciprocating the carriages 20 and 26 in timed relation with the screw 14 as well as the mechanism for moving the plunger 28 downwardly at the beginning of the test area and upwardly at the end of the test area are described in U.S. Pat. Nos. 3,387,704 and 3,557,950 to Powers. Further description thereof is unnecessary. Each of the plungers 18 and 28 is cammed or spring-biased into contact with the container 15 at the beginning of the stroke of the carriages and biased away from the container at the end of the carriage strokes.

Figure 2:
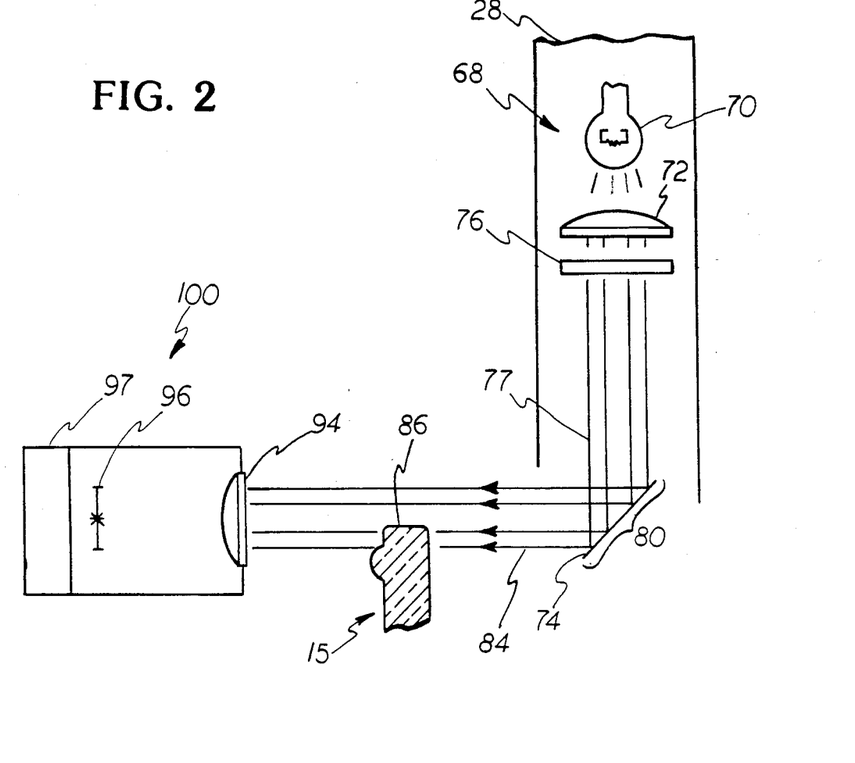
FIG. 2 is an enlarged, fragmentary schematic diagram of the finish leak detector of FIG. 1.

Focusing now on the present invention as illustrated in FIGS. 1 and 2, the finish leak detector 11 comprises an illumination assembly 68 supported by the plunger 28 for vertical reciprocations therewith into and out of the mouth of bottle 15. When the bottle 15 arrives at the inspection site, the plunger 18 is extended so that the rollers 16 urge the bottle 15 against the rotation belt 4 to begin rotation of the bottle 15. Simultaneously, the plunger 28 is lowered such that the illumination assembly 68 is lowered into the mouth of the bottle 15 to the position illustrated in FIGS. 1 and 2. Illumination assembly 68 comprises a light source 70 which may be a simple incandescent light bulb, a lens 72 to collect the light of the source 70 and focus it downwardly toward a mirror 74 (or alternately, a prism) also within the illumination assembly 68. The assembly 68 further comprises a diffuser 76 supported between the lens 72 and the mirror 74 to diffuse the light emanating from the source 70 to produce a substantially collimated and uniformly intense light beam 77 which illuminates the mirror 74 over region 80. The cross section of the light beam 77 is broad enough and the angle of the mirror 74 is such that the light reflects horizontally as indicated by arrows 84 above and below a sealing surface 86 of the bottle 15.

The finish leak detector 11 further comprises a camera 100 which is fixedly attached to the carriage 20 by a support 92 for reciprocal movement with the carriage 20 in the direction of and the direction opposite the conveyor 12. Consequently, the camera 100 tracks the bottle 15 at the inspection site. The camera 100 comprises a lens 94 which receives the light reflected by the mirror 74, collects it and focuses it upon a vertically oriented, linear array 96 of charge coupled devices, which array is also located within the camera 100. By way of example, the linear array contains 256 pixels which allows for 1/16" depth to the defect plus or minus 1/16" tolerance with a resolution of 0.0007" per pixel. Also by way of example, the linear array 96 may comprise a Fairchild CCD111 model line-scan sensor which is also sold under the trademark I-Scan. The camera 100 also includes electronics 97 to process the outputs of the charge coupled devices. As described in more detail below, the camera detects the heights of the sealing surface at a multiplicity of points as the bottle is rotated, and deviations such as depressions in such heights indicate sealing surface defects.

Figure 3:
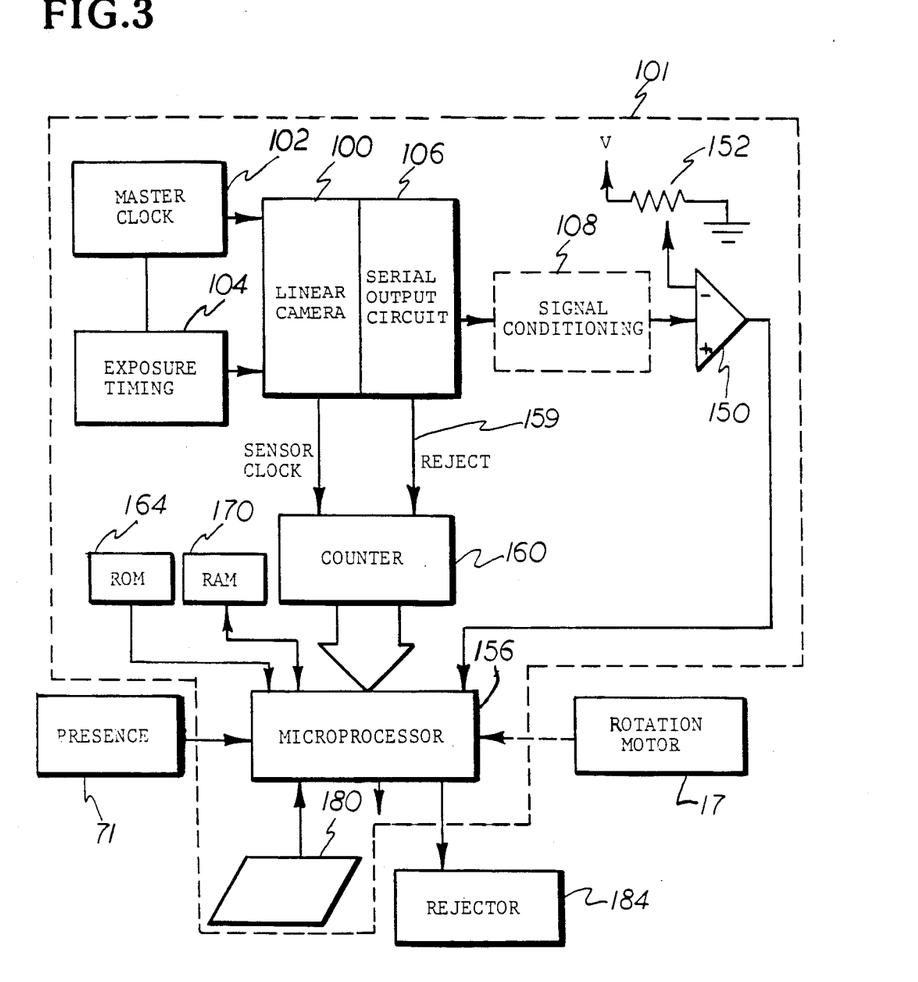
FIG. 3 is a schematic block diagram of electronic circuitry within the finish leak detector of FIG. 1.
Figure 4:
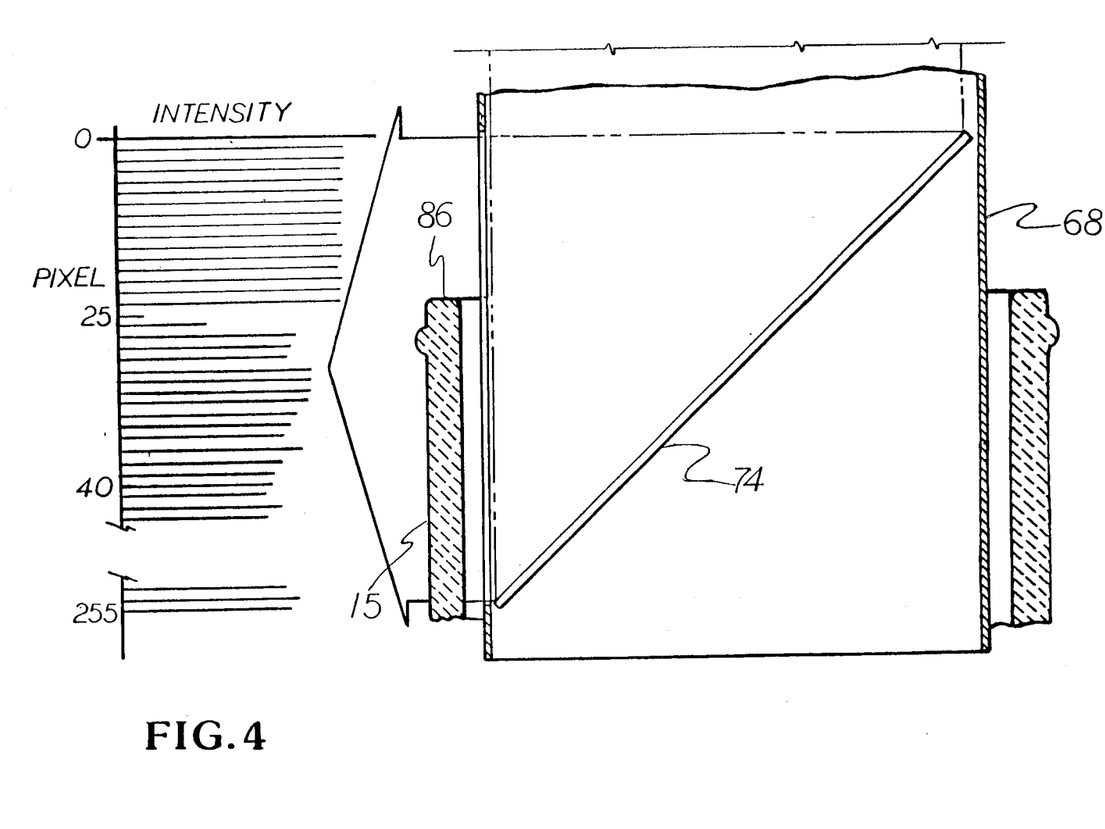
FIG. 4 is a graph illustrating the response of a camera within the finish leak detector of FIG. 1 during an inspection operation.

The camera 100 is part of a video processor and control 101 illustrated in FIGS. 1 and 3 which processor operates from a master clock 102. The video processor 101 also includes an exposure timing element 104 which sets an exposure or integration time for the linear array 96. In order not to mix two lines of video information in the linear array 96, the exposure time must be greater than the time necessary to read all the information from the previous line. The camera 100 supplies three outputs, video clock, start of scan and binary video, to a serial output circuit 106 which outputs serially analog data indicative of the intensity of the illumination on each of the pixels. The analog output of the circuit 106 is fed into a signal conditioning circuit 108, the output of which is illustrated in FIG. 4 for one profile of the bottle mouth. In the illustrated embodiment, the "zero-th" pixel of the linear array 96 is the highest one and the 255th pixel is the lowest one according to the orientation of FIG. 1. As further illustrated in FIG. 4, pixels 0–255 are illuminated to some degree by the light beam 84 transmitted by the illumination assembly 68. Pixels 0–24 are illuminated by a portion of the beam 84 which is entirely above the sealing surface 86 so that the pixels 0–24 receive approximately a maximum intensity level of light and such is indicated by the relatively large height of the graph for the pixels 0–24. The intensity of the light received by the pixel 25 is the smallest of the linear array because such pixel is aligned horizontally with the sealing surface 86. Consequently, light transmitted at that level toward the pixel 25 is reflected by the surface 86 away from the pixel 25 due to either minor irregularities to the sealing surface 86 or lack of parallel between the sealing surface 86 and the beam 84 such that the light beam reflects from the sealing surface 86 according to Snell's law. The pixels 26–255 are located below the level of the sealing surface 86 and receive an intensity level which is substantially greater than the level received by the pixel 25 because the light beam 84 below the sealing surface 86 is transmitted through the finish portion which is generally transparent. Irregularity in the intensity levels observed by the pixels 26–255 may be due to irregularities in the cross-section of the finish portion such as due to threads in the finish. Irregularities in the heights of the pixels 0–255 may also be due to upward and downward vibrations. It should be noted that as the bottle 15 is rotated, the video camera 100 continuously outputs the intensity levels experienced by the pixels in the linear array 96, and the height of the sealing surface 86 at the intersection of the light beam 84 is indicated by the position of the pixel which receives the lowest intensity level. For example, if the graph of FIG. 4 represents a normal portion of the sealing surface 86, the corresponding graph of the profile of a "dipped" portion would indicate that a higher numbered pixel, that is, a pixel below the 25th one is the one having the lowest intensity level. By way of example, if the resolution for a pixel is 0.0007" and the bottle was in a position such that the beam 84 passes through the bottle finish at the lowest depth of a 0.007" dip, then pixel 35 would indicate the lowest intensity level.

The output of signal conditioning converter 108 is supplied to one input of a comparator 150. The other input of the comparator is supplied by a potentiometer 152 to yield a threshold level which is set above the intensity level corresponding to the sealing surface 86 (the height of the intensity bar of the 25th pixel in FIG. 4) but less than the other intensity levels of the other pixels (less than the intensity level of the pixel 26). Consequently, the output of the comparator 150 goes low when the signal conditioning circuit 108 inputs to it the intensity level of the pixel corresponding to the height of the sealing surface 86, in the aforesaid example, pixel 25. The low level signal output from the comparator 150 is supplied to an input of a microprocessor 156 within the video processor and control 101. Upon receipt of the low level signal, the microprocessor reads the output of a counter 160 within the video processor 101 which counter is incremented by the master clock from count zero for each serial output representing the intensity level observed by each of the pixels. Consequently, in the aforesaid example, when the output of the comparator 150 goes low, the counter provides a count of 25 to the microprocessor 156 so that the microprocessor learns the height of the sealing surface 86. By way of example, the serial output circuit 106 and the counter 160 may be provided by a Fairchild Pixel Locator Model CCD1120-02. The serial output circuit also resets the counter via a line 159 after all of the pixels of a scan have been output by the serial output circuit.

Figures 5, 11:
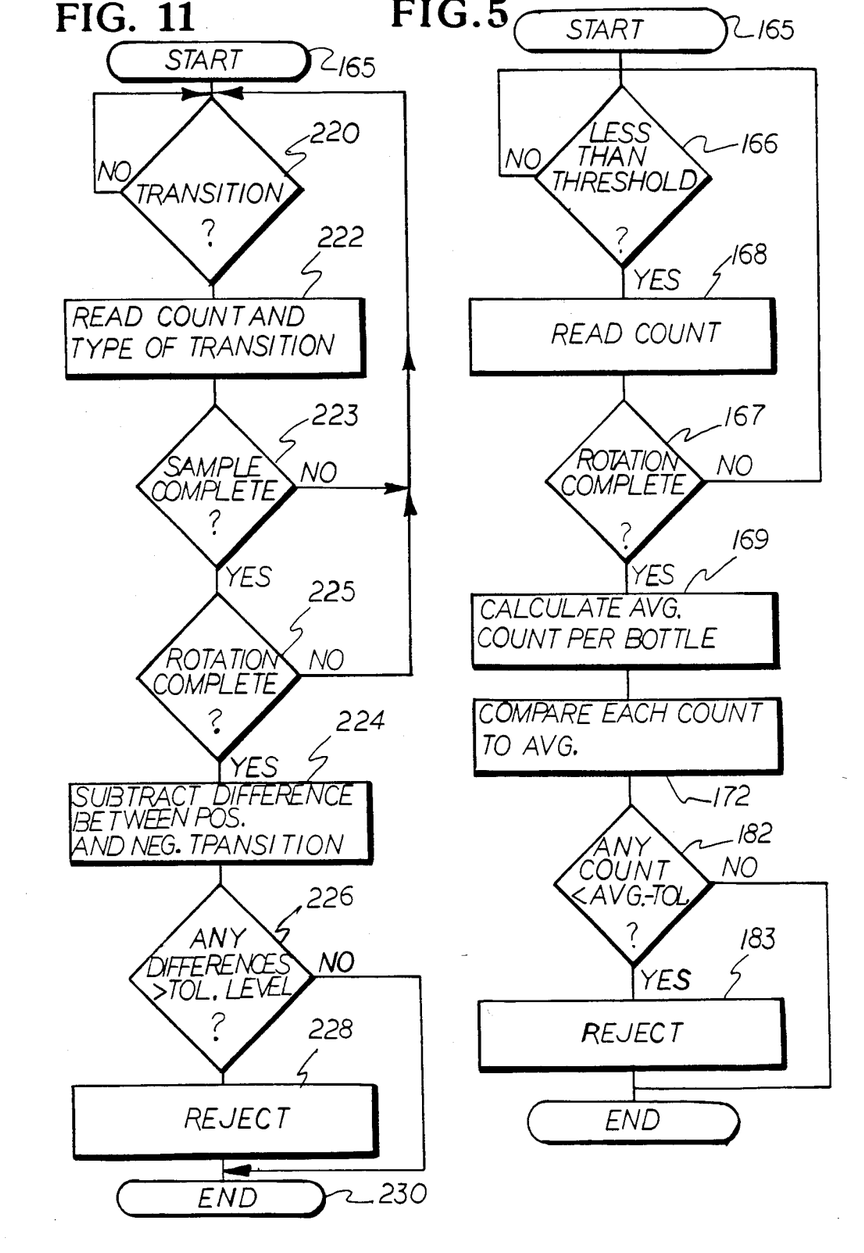
FIG. 5 is a flow chart illustrating the operation of a microprocessor within the finish leak detector of FIG. 1 during an inspection operation.
FIG. 11 is a flow chart illustrating the operation of a microprocessor within the finish leak detector of FIG. 6 during an inspection operation.

The operation of the microprocessor 156 is illustrated by a flow chart of FIG. 5 representing a computer program or firmware within a read-only memory (ROM) 164 within the video processor and control 101. The microprocessor starts (step 165) when a presence sensor (not shown) coupled to the auger 14 is activated, indicative of the arrival of the bottle 15 at the test area. Then the microprocessor periodically reads the input supplied by the output of the comparator 150 (step 166) and when the output goes low, reads the output of the counter 160 as noted above (step 168) and then stores the count in a random access memory (RAM) 170. This count corresponds to the height of the bottle sealing surface. The microprocessor continues to monitor the output of the counter and read additional counts until the bottle has been rotated once (step 167) (or alternately, during a longer, predetermined inspection interval). The completion of the rotation is indicated by a shaft encoder on the rotation motor 17. Then, the microprocessor calculates the average count per bottle for the multitude of samples of the bottle, which calculation represents the average height of the sealing surface 86 over 360° (step 169), and stores the average count in the RAM 170. Then, the microprocessor compares each of the counts stored in the RAM 170 to the average count calculated in the step 169 (step 172). If any of such counts are less than the average count minus a tolerance value, which is entered into the microprocessor via a keyboard 180 (FIG. 1) (or alternately via a thumb wheel switch, etc.), then the microprocessor activates a rejector 184 (step 182) because such count indicates that a portion of the sealing surface 86 is well below the average height, a characteristic of either a dip, a saddle or a leaner. If no such count is less than the average count minus the tolerance, then the step 182 leads to the end step without activation of therejector 184. This indicates an acceptable sealing surface.

It should also be noted that the aforesaid circuitry and process detect leaning bottles because the sealing surface of a leaning bottle generally leans along with the bottle so that one portion of the sealing surface in the leaning bottle is substantially below the average height. If desired, the microprocessor can be programmed to distinguish leaning bottles from dips by calculating the number of successive samples having a sealing surface height substantially less than the average. A very large number corresponding to approximately half the finish circumference indicates lean.

Figure 6:
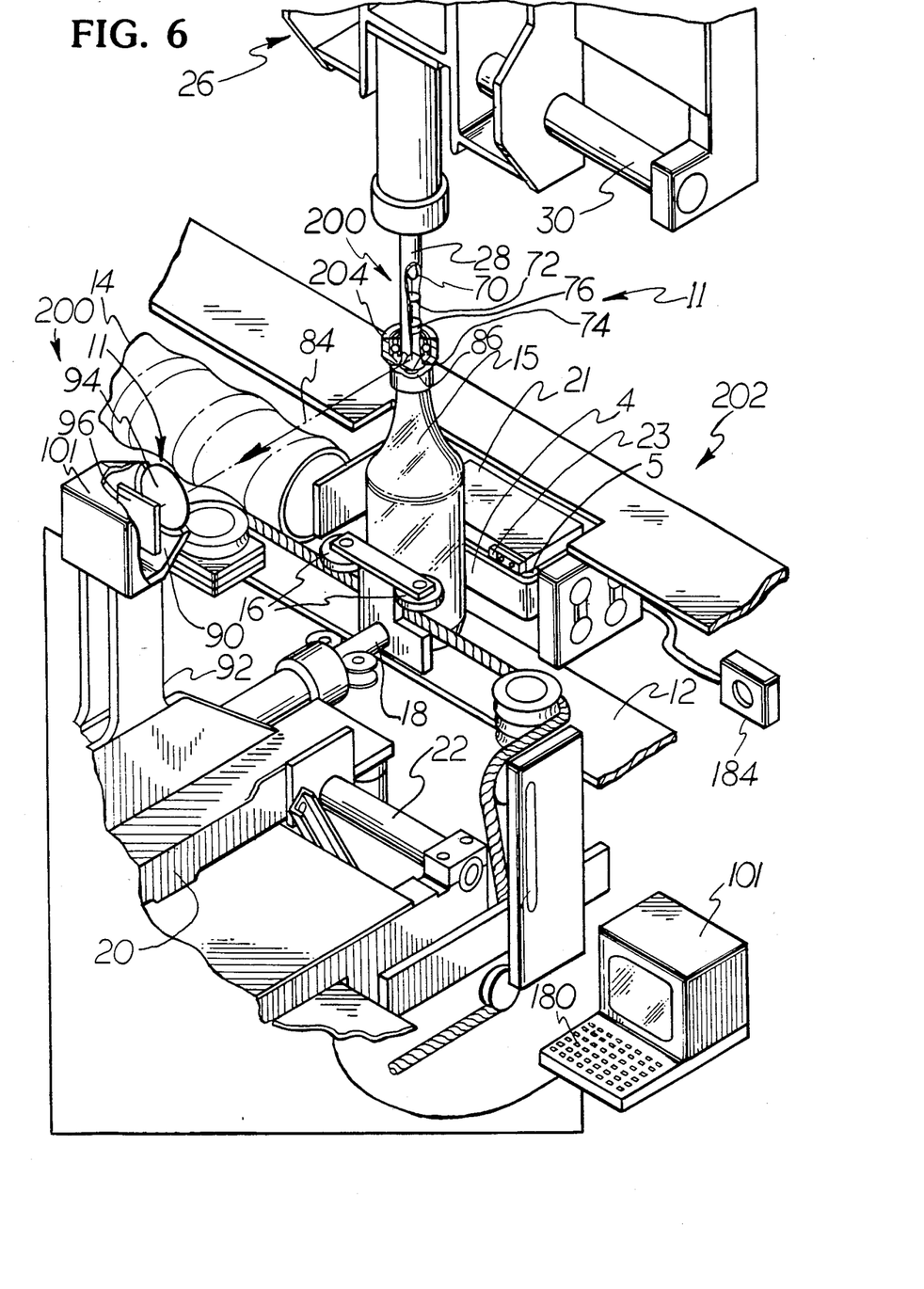
FIG. 6 is a perspective view illustrating another inspection system including another finish leak detector embodying the present invention.
Figure 7:
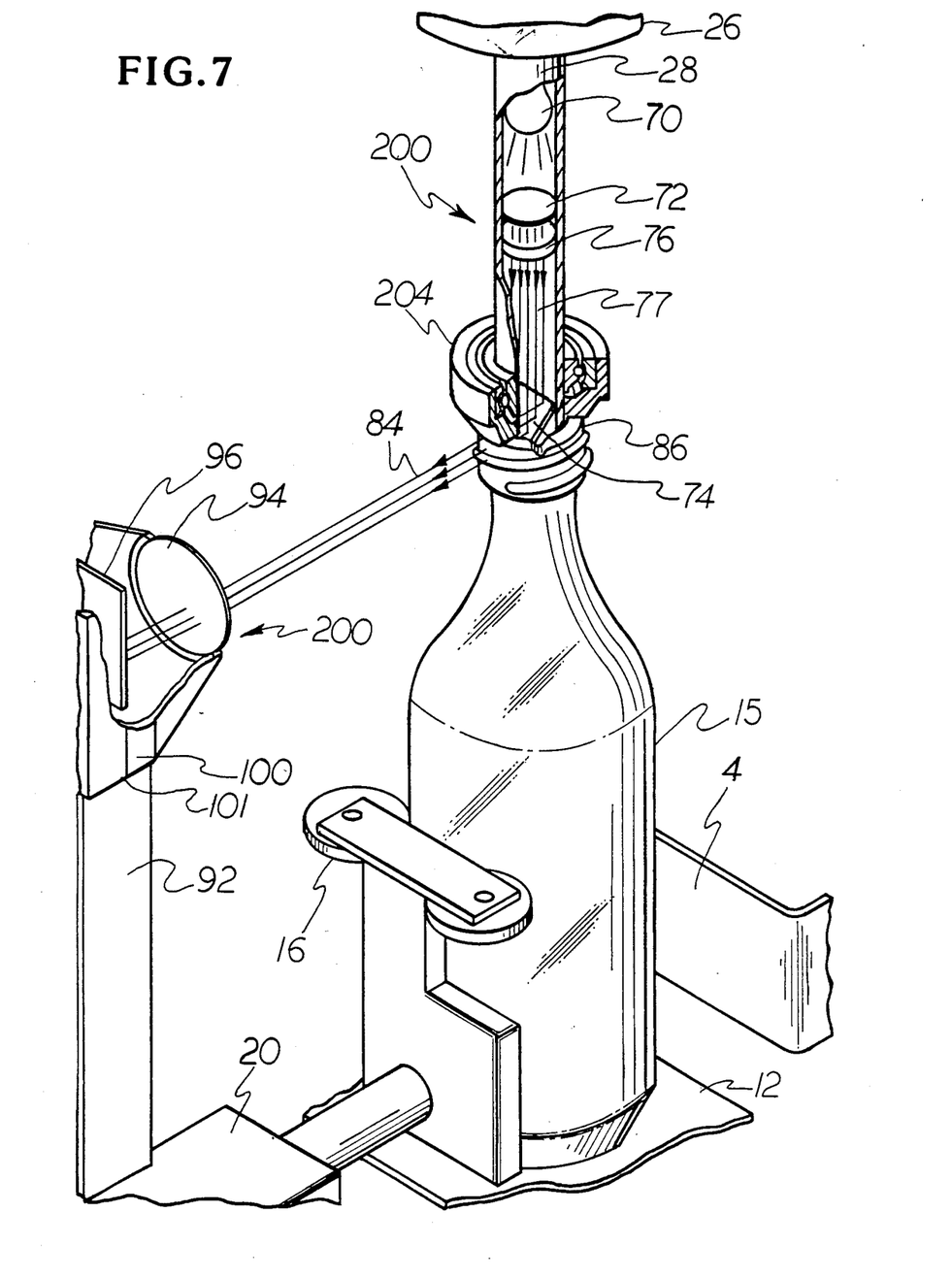
FIG. 7 is an enlarged, fragmentary perspective view of the inspection system of FIG. 6 including the other finish leak detector embodying the present invention.
Figure 8:
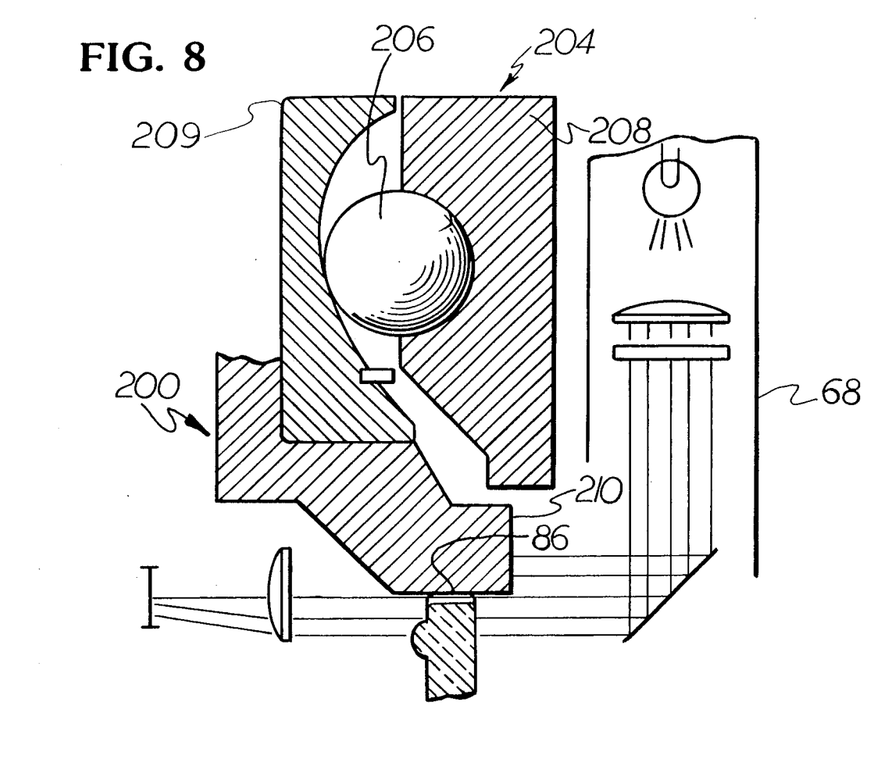
FIG. 8 is an enlarged, fragmentary schematic view of the finish leak detector of FIG. 6.
Figure 9:
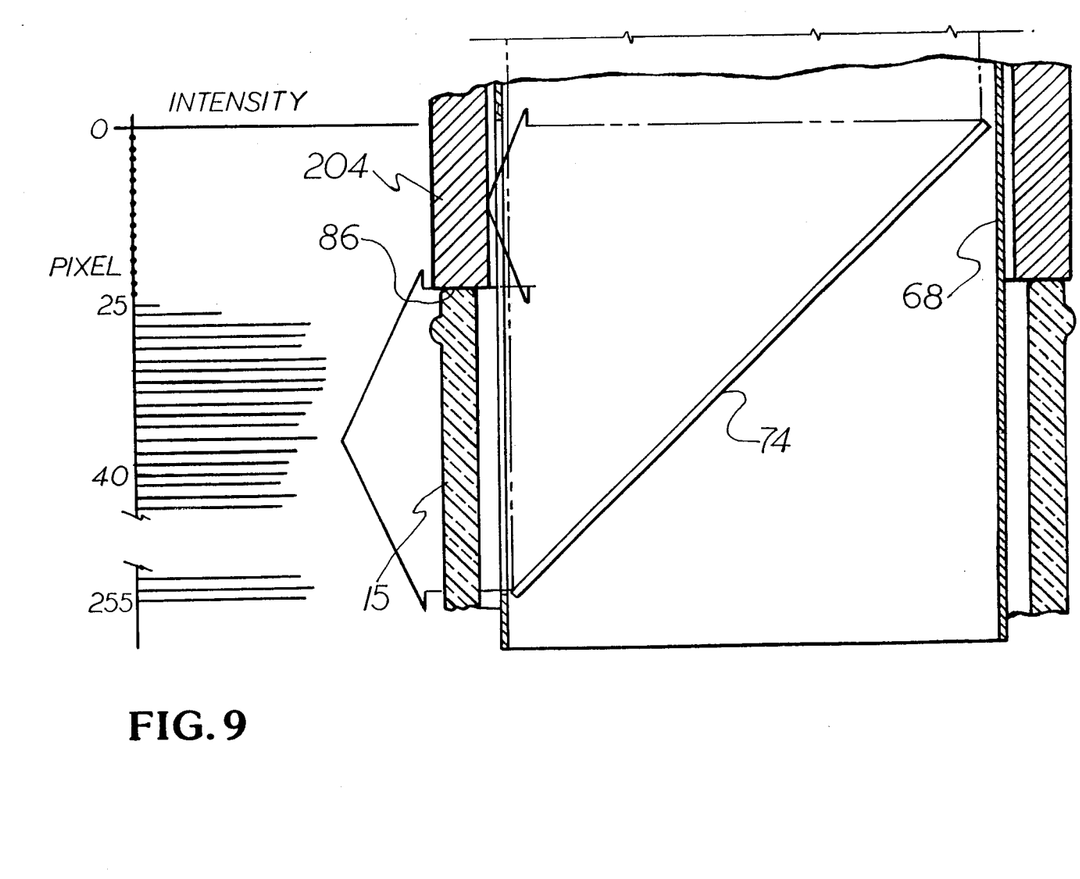
FIGS. 9 and 10 are graphs illustrating the responses of a camera within the finish leak detector of FIG. 6 during an inspection operation.

FIGS. 6, 7 and 8 illustrate another finish leak detector 200 also embodying the present invention. The finish leak detector 200 is adapted to an inspection system 202 which is very similar to the inspection system 10 illustrated in FIG. 1 and like reference numerals indicate like components. The finish leak detector 200 is also similar to the finish leak detector 11 with like reference numerals indicating like elements. The basic differences between the two finish leak detectors are as follows. The finish leak detector 200 includes a bearing mounted head 204 which circumferentially surrounds the illumination assembly 68 and bears against the entire sealing surface 86 of the bottle 15. The bearing mounted head 204 includes a ball joint comprising a ball bearing 206, an inner race 208 and an outer race 209. The inner race 208 is fixedly attached to the plunger 28 so that the socket can seat on the sealing surface 86 despite a limited amount of lean of the sealing surface. The bearing mounted head also includes a bearing member 210 which engages the sealing surface 86 and is stationary relative thereto during rotation of the bottle. Consequently, the bearing member 210 rotates relative to the outer race 209 during rotation of the bottle. The bearing mounted head serves two functions. It helps to stabilize the bottle 15 against vertical vibrations so that the pixel which corresponds to the height of the sealing surface during each sample is less affected by vibrations. Also, the bearing mounted head provides a reference level indicative of the non-defective or prevailing height portions of the sealing surface 86. As illustrated by the graph of FIG. 9 which represents a profiled portion of the bottle mouth which is normal, and in fact corresponds to the profiled portion of FIG. 4, the intensity level observed by each of the pixels 0-24 located above the sealing surface 6 is zero except for ambient light because the portions of the light beam 84 located above the sealing surface 86 are blocked by the bearing mounted head. The pixel 25 located at the level of the sealing surface 86 receives a very small amount of light which is comparable to the amount of light received by the pixel 25 in the example of FIG. 4. The pixels 26-255 located below the height of the sealing surface 86 receive light which is transmitted through the finish portion of the bottle and the amount of light received by each of the pixels 26-255 in the FIG. 9 example is approximately the same as each of the pixels 26-255 in the FIG. 4 example. As illustrated in FIG. 9, the first or lowest numbered pixel which exhibits a significant intensity level represents the height of the undersurface of the bearing mounted head and this height is the normal height or prevailing height of the sealing surface 86. The bearing element 210 is not compliant enough to follow the contour of a dip or even a saddle.

Figure 10:
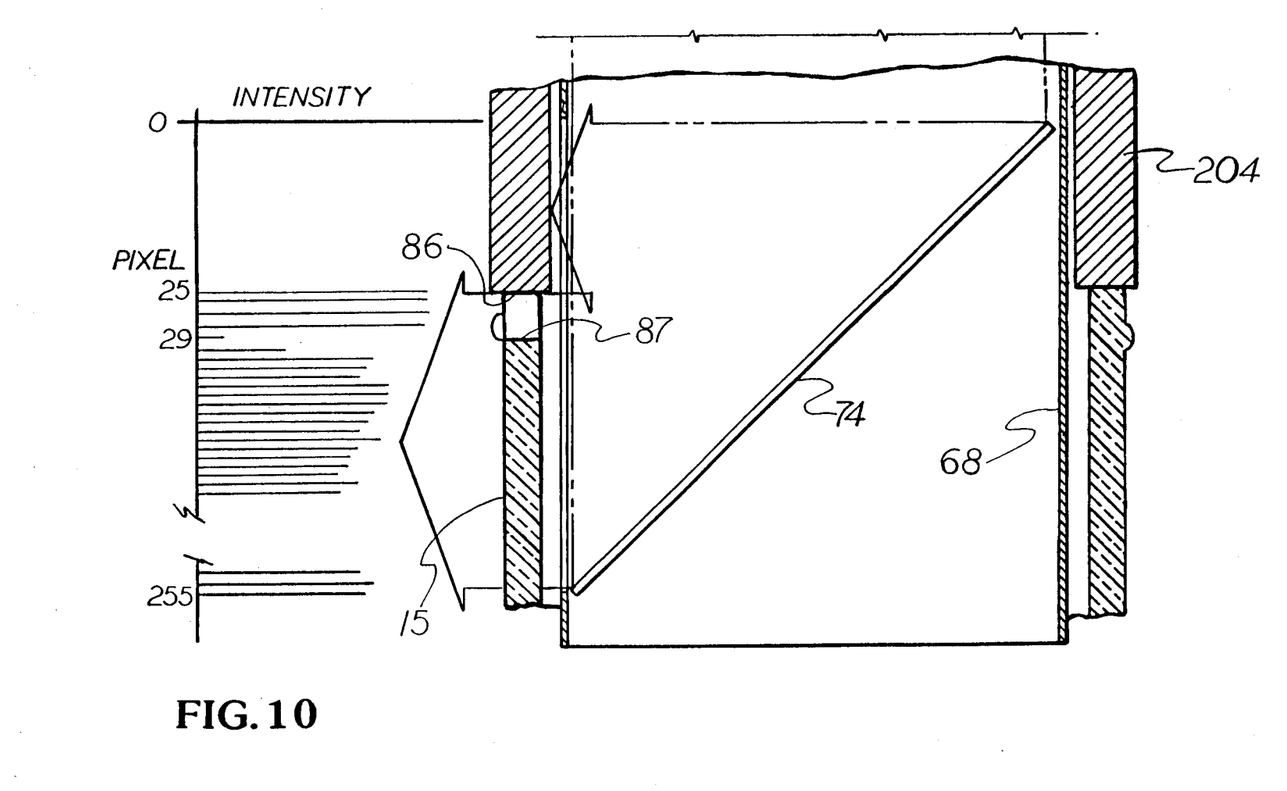

FIG. 10 illustrates the intensity graph of a profiled portion of the bottle finish corresponding to a dip 87 (or a saddle). For reasons noted above, the height of the pixel 25 represents the undersurface of the bearing element 210 or the normal or prevailing height of the sealing surface. The graph also illustrates that the four pixels below the undersurface of the bearing element 210, pixels 25–28, receive a very high light intensity indicative of a gap beneath the bearing element 210. The next pixel down, pixel 29, exhibits the low intensity level associated with the height of the sealing surface at the profile of the sample so that the gap between the undersurface of the bearing element 210 and the sealing surface 86 at this profile is approximately four pixels wide. The pixels beneath the pixel 29 receive the light intensities as noted above associated with the column 84 being transmitted through the bottle finish. The finish leak detector 200 utilizes the same video camera 100 and the same video processor and control 101, as noted above for the finish leak detector 10 except that the ROM 164 within the finish leak detector 200 contains a slightly different operating program or firmware as illustrated in FIG. 11. When the presence sensor indicates that the bottle 15 has arrived at the inspection site (step 165), the microprocessor periodically reviews the output of the comparator 150. Whenever the output makes a transition in either polarity (step 220) the microprocessor reads the output of the counter 160 and stores this count and the type of the transition (step 222). The microprocessor continues to note counts and transitions until the sample is complete, i.e., when the count reaches 255 (step 223). It should be noted that for the samples in which the profiled portion does not include a dip or a saddle, there is but one transition corresponding to the transition from an approximately zero intensity level pixel to a pixel having an intensity level greater than zero as illustrated in FIG. 8. However, where a sample is a profiled portion including a dip or saddle, there will be a first transition corresponding to the transition from a zero intensity pixel to a greater than zero intensity pixel, a second transition from a high intensity pixel to a very low intensity pixel corresponding to the height of the sealing surface, and a third transition corresponding to the transition from the very low intensity level pixel of the sealing surface to the relatively high intensity level pixel below. The microprocessor repeats the steps 220–223 for additional samples or profiles of the bottle finish until one rotation has been completed (step 225).

Next, the microprocessor subtracts the difference in counts between the first positive going transition and the first negative going transition (step 224) which indicates the gap between the undersurface of the bearing element 210 or prevailing height of the sealing surface and the lowest depth of the sealing surface 86 beneath it in the profiled portion. This is the depth of the dip or saddle, and if it is greater than a tolerance level (step 226) input previously to the microprocessor via the keyboard 180, the microprocessor activates the rejector 184. If not, the bottle is determined to have an adequate sealing surface.

Thus, the bearing mounted head serves as a reference level to gauge the depth of dips or saddles and the performance of the finish leak detector 200 is not substantially affected by vibrations.

By the foregoing, finish leak detectors embodying the present invention have been disclosed. However, numerous modifications and substitutions may be made without deviating from the scope of the invention. For example, if desired, finish rollers illustrated in the U.S. Pat. No. 3,690,456 to Powers may be utilized in conjunction with the finish leak detector 11 to stabilize the bottle 15 against vibrations; such finish rollers should not be positioned in the path of the light beam 84 and should not otherwise affect the process carried out by the electronic control 158 associated with the finish leak detector 10. Also, the finish leak detectors 11 and 200 can also be used to detect raised "bumps" in the sealing surface. Therefore, the invention has been disclosed by way of illustration and not limitation and reference should be made to the following claims to determine the scope of the invention.

I claim:

1. An apparatus for inspecting the sealing surface of a vertically standing bottle having a mouth portion at the top thereof comprising
    means for horizontally projecting a collimated and uniformly intense light beam having a selected vertical height including
    light source means for producing a vertically downwardly directed substantially collimated and uniformly intense light beam and
    mirror means having a selected size and being supported at a predetermined angle for reflecting said light beam as a horizontal substantially collimated and uniformly intense light beam having a selected vertical height,
    means for downwardly vertically displacing said mirror means from a location vertically above the bottle to be inspected to a position whereat a portion of said mirror means is located within the bottle whereby a portion of said horizontal light beam will pass through one wall of the bottle amd the remaining portion will pass above the bottle,
    means outside of the bottle for receiving said horizontal collimated beam,
    means outside of the bottle so that said receiving means will receive said horizontal beam as it passes through horizontally continuous portions of the top of the bottle, and
    means for comparing the received light beam with a standard as the bottle is rotated to identify an imperfection in the top surface of the bottle finish.

2. An apparatus according to claim 1 wherein said light source means comprises a light source.

3. An apparatus according to claim 2 wherein said light source means further comprises lens means for collecting the light from said light source and focusing the collected light toward said mirror means.

4. An apparatus according to claim 3, wherein said light source means further comprises means for diffusing the focused light into a collimated and uniformly intense beam of light.

* * * * *